United States Patent

McCulloh

[19]

[11] Patent Number: 5,915,834
[45] Date of Patent: Jun. 29, 1999

[54] VARIABLE SET POINT OXYGEN CONCENTRATION MIXER

[75] Inventor: Kevin G. McCulloh, Davenport, Iowa

[73] Assignee: Litton Systems, Inc., Davenport, Iowa

[21] Appl. No.: 08/871,320

[22] Filed: Jun. 9, 1997

[51] Int. Cl.⁶ .................................................. A61M 16/00
[52] U.S. Cl. .................................... 366/151.1; 366/160.1; 366/182.4; 128/204.22; 128/205.11
[58] Field of Search .............................. 366/107, 151.1, 366/152.1, 142, 140, 160.1, 162.1, 182.1, 177.1, 179.1; 128/203.12, 203.25, 203.26, 204.22, 204.21, 205.11, 200.24, 204.18; 137/88

[56] References Cited

U.S. PATENT DOCUMENTS

| | | | |
|---|---|---|---|
| 3,667,463 | 6/1972 | Barnes | 128/203.16 |
| 3,727,626 | 4/1973 | Kanwisher et al. | 137/88 |
| 3,922,149 | 11/1975 | Ruder et al. | 95/22 |
| 4,015,617 | 4/1977 | Connolly | 137/88 |
| 4,587,967 | 5/1986 | Chu et al. | 128/205.11 |
| 4,919,132 | 4/1990 | Miser | 128/205.17 |
| 5,593,478 | 1/1997 | Hill et al. | 96/111 |
| 5,632,268 | 5/1997 | Ellis et al. | 128/204.18 |

*Primary Examiner*—Tony G. Soohoo
*Attorney, Agent, or Firm*—Michael H. Wallach

[57] ABSTRACT

Apparatus for mixing two gasses, at least one of which contains oxygen, to a desired concentration of oxygen, comprising a mixing plenum, an inlet valve, for admitting one of the two gasses into the mixing plenum, an oxygen sensor for detecting oxygen concentration of mixed gasses in the mixing plenum and in response generating an output signal representative thereof, and a controller for receiving the output signal and a user input representing the desired concentration of oxygen, comparing the oxygen concentration of the mixed gasses represented by the output signal to the desired concentration of oxygen, and in response controlling the inlet valve to regulate flow of respective ones of the two gasses into the mixing plenum and thereby maintain the desired concentration of oxygen.

29 Claims, 4 Drawing Sheets

VARIABLE SET POINT OXYGEN CONCENTRATION MIXER

FIELD OF THE INVENTION

The present invention relates in general to gas mixing devices, and more particularly to an apparatus for mixing two gases, at least one of which contains oxygen, to a desired concentration of oxygen purity.

BACKGROUND OF THE INVENTION

Gas mixing devices are generally divided into three categories: mass flow controlled blending devices, partial pressure mixing devices, and mass weight control mixing devices.

Current gas mass flow controlled mixing devices for mixing oxygen with air or nitrogen, are expensive and require precise knowledge and control of the two gasses before being mixed together. Any variation from the known concentrations of the gasses prevents an accurate mixing of the gasses to a desired oxygen concentration.

Partial pressure gas mixing devices require extensive operator interface and, as with gas mass flow controlled devices also require extensive knowledge and control of the exact oxygen concentrations before mixing of the gasses. Furthermore, these devices suffer from latent inaccuracies in mixing of the gasses.

Devices which mix gasses by means of mass weighing also require precise knowledge of the two gasses being mixed and expensive weighing and control devices.

As indicated above, each of the above discussed prior art devices requires accurate knowledge of the input gasses and expensive analysis and display of oxygen content after mixing to ensure accuracy. These devices are also often susceptible to pressure and temperature sensitivity.

SUMMARY OF THE INVENTION

According to the present invention, an apparatus is provided for automatically monitoring and mixing two gasses (oxygen and air, oxygen and nitrogen, or nitrogen and air) to a desired concentration of oxygen purity. The apparatus of the present invention allows a user to "dial in" the desired oxygen concentration by means of a keypad and to vary the concentration from 0% to 100% oxygen. There are no mixing errors due to inaccuracies in the inlet gas concentrations, as in prior art devices, as a consequence of the method by which the gasses are mixed. The mixed gas is monitored and the mixing process is automatically controlled until it reaches the desired oxygen purity set point.

The apparatus of the present invention overcomes many of the problems associated with the above discussed prior art gas mixing devices by monitoring the gasses as they are mixed and controlling the mixing process until the desired oxygen purity set point is reached. There is no requirement for precise stable gas sources for the device or complicated user interfaces, as with prior art devices. Oxygen concentration is accurately monitored, displayed and adjusted according to the apparatus of the present invention. Any mixed product gas that is not within the limits of the set point is purged to the atmosphere to ensure that only product gas of the desired concentration is output from the device.

The gas mixing device of the present invention has many applications, from the filling of scuba tanks for technical diving, filling of oxygen bottles for medical use, to industrial applications requiring specialty mixed oxygen gas.

BRIEF DESCRIPTION OF THE DRAWINGS

A detailed description of a preferred embodiment of the invention is provided herein below, with reference to the following drawings in which.

DETAILED DESCRIPTION OF THE PREFERRED EMBODIMENT

Figure 1:
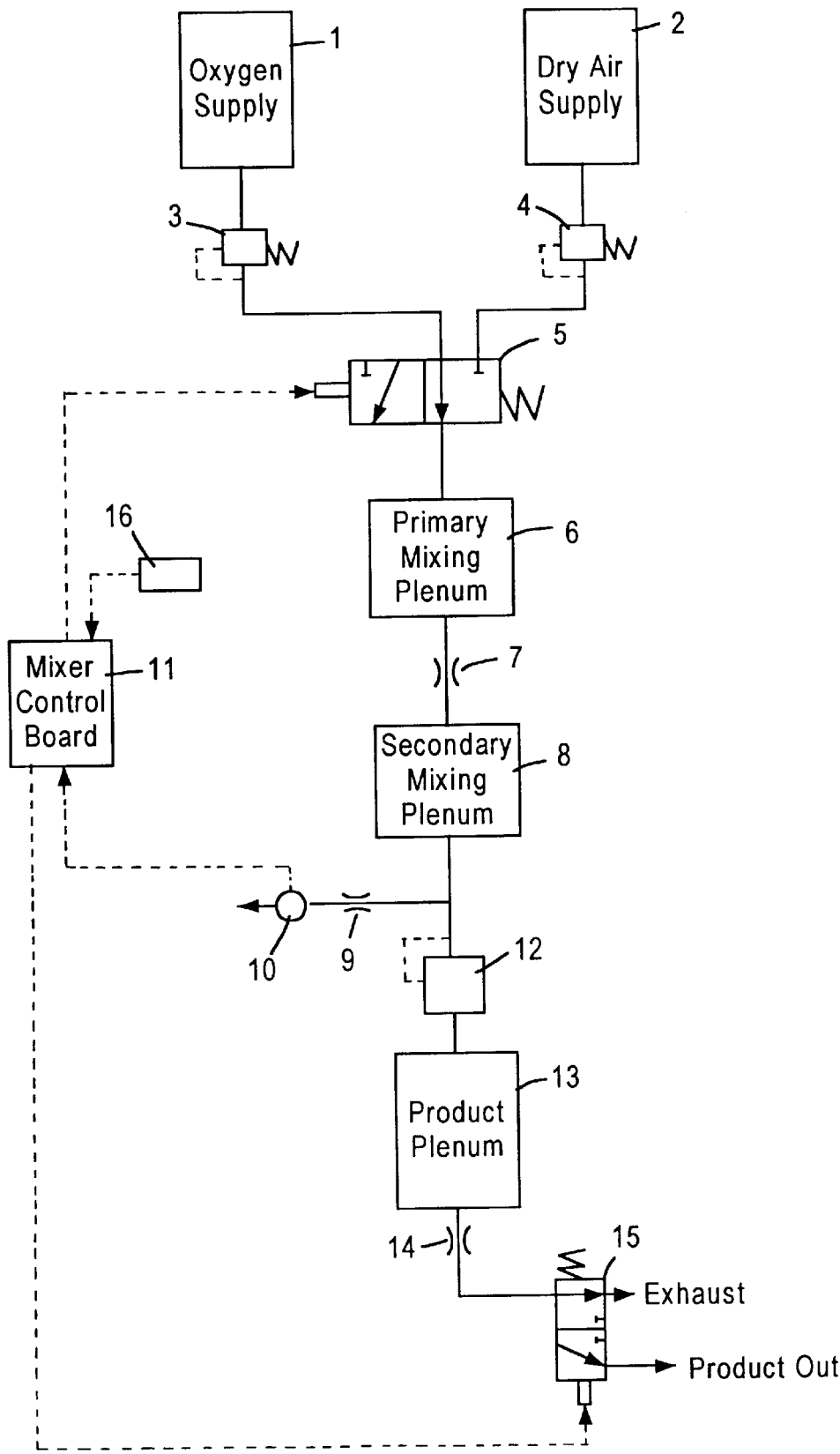
FIG. 1 is a schematic diagram of the gas mixing device according to the preferred embodiment.

The sequence of operation is described herein with reference to FIG. 1 and an example wherein a combination of air and oxygen are used, although air and nitrogen or nitrogen and oxygen could be used as the inlet gas source. An inlet oxygen supply source (1) and an inlet air supply source (2) are connected to the inlet of the mixing device of the present invention. The oxygen supply gas flows through an inlet oxygen regulator (3). The air supply gas simultaneously flows through the inlet air regulator (4).

Figure 2:
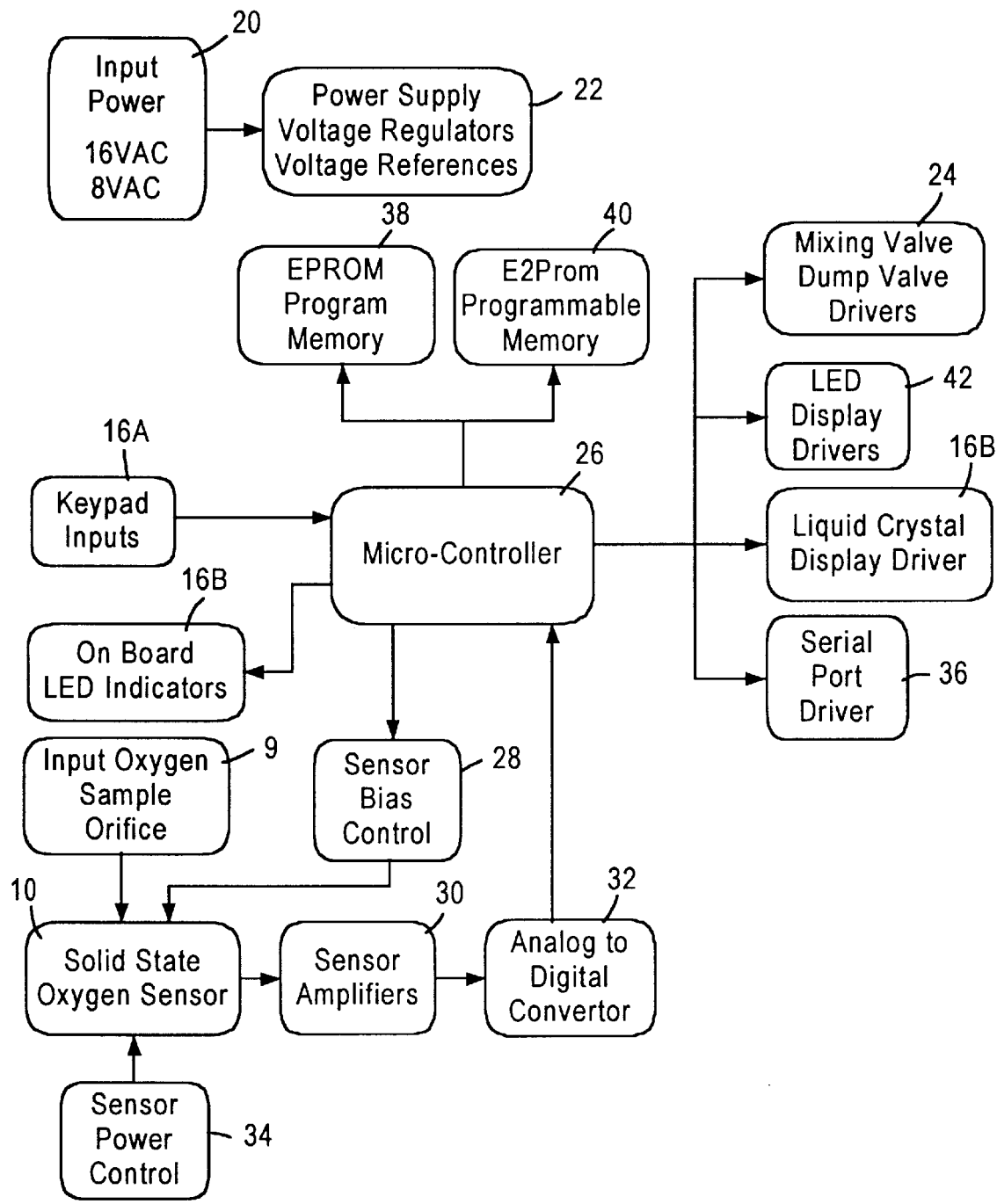
FIG. 2 is a block diagram of the control board for the device shown in FIG. 1.
Figure 3:
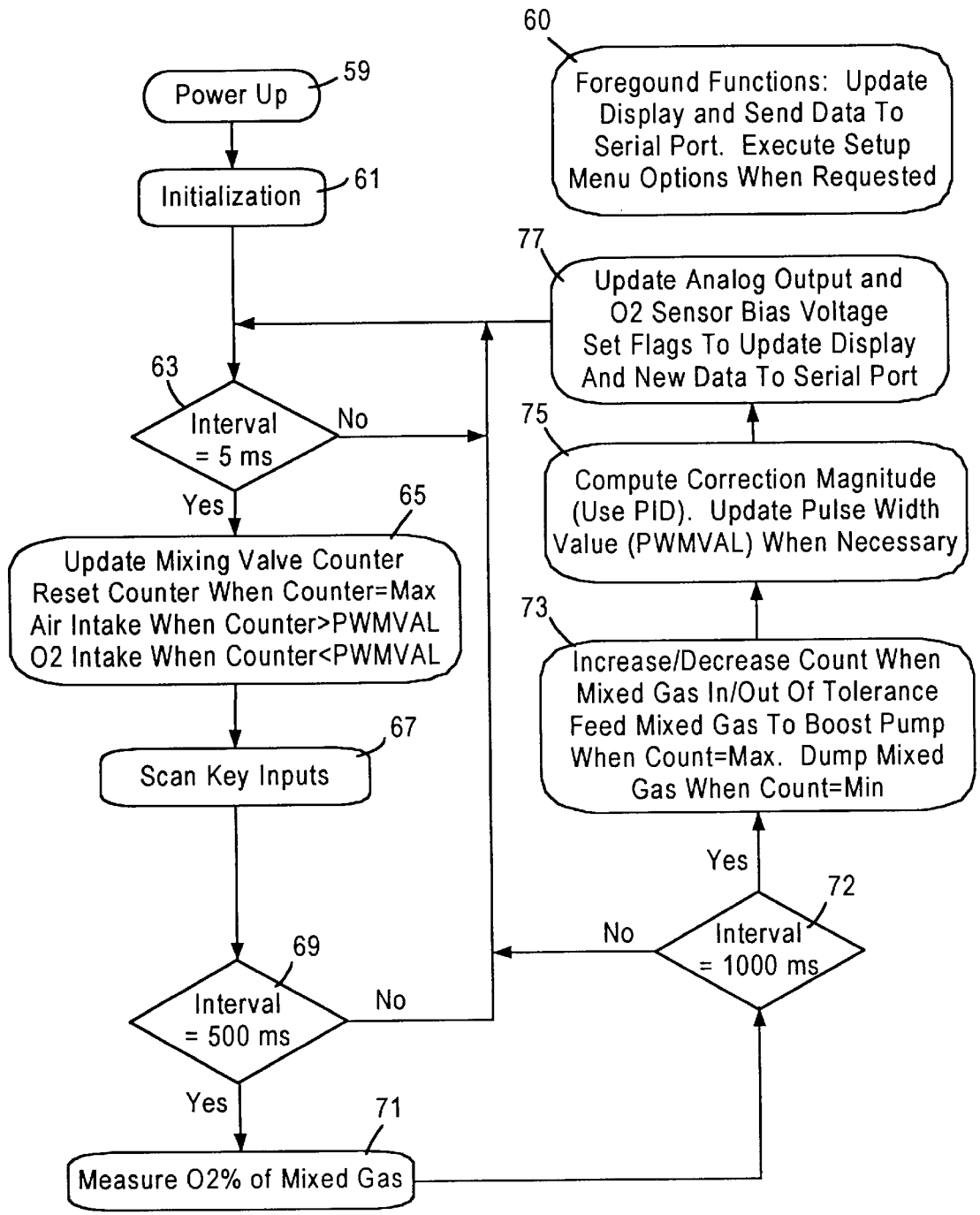
FIG. 3 is a flowchart showing operation of the control board in FIG. 2.

After the operator turns on the electrical power to the device in order to start operation (see input power source (20) and power supply (22) in FIG. 2 and step 59 in FIG. 3), the control board (11) runs through an initialization and warm up sequence (step 61), the sensor goes through a several minute warm up period, (step 63) and then the output display (16) displays the current operating mode, on-off status, current oxygen concentration, and current oxygen set points. Oxygen set point changes are made by performing keypad sequences that prompt the user through the menu, as shown at (16A) and (16B) in FIG. 2, and foreground function 60 of FIG. 3. Once the desired oxygen concentration has been set, the mixer control board (11) cycles the mixing valve (5) between the inlet air supply and the inlet oxygen supply via mixing valve driver (24) in FIG. 2. The air and oxygen flow from the mixing valve (5) into the primary mixing plenum (6) where the oxygen and air mix. The gas then flows though a flow control orifice (7) into the secondary mixing plenum (8) to further blend the gasses.

A small portion of the mixed gas flows through orifice (9) into the oxygen sensor (10) which senses the oxygen concentration and sends a signal to the mixer control board (11). As shown in FIG. 2, operation of the control board (11) is governed by a micro-controller (26), which sends signals to a sensor bias control circuit 28 of the sensor (10). The signal output from sensor (10) is first amplified by sensor amplifiers (30) and digitized via an analog to digital converter (32). A sensor power control (34) is further provided to regulate operation of sensor (10).

The mixer control board (11) compares the signal from the oxygen sensor (10) to the desired oxygen concentration setpoint. The mixer control board (11) determines whether more oxygen or air is needed to reach the desired set point, and then controls the length of time that the mixing valve (5) is flowing oxygen or air. For example: If the oxygen concentration from the sensor is lower than the desired oxygen set point, the mixer control board (11) increases the amount of time that the mixing valve (5) is in the oxygen flow position and decreases the amount of time by an equal amount that the mixing valve is in the air flow position. These times are constantly adjusted by the mixer control board until the gas mixture is within the acceptable limits of plus or minus 0.25% oxygen or any limit that is determined to be acceptable.

Figure 4:
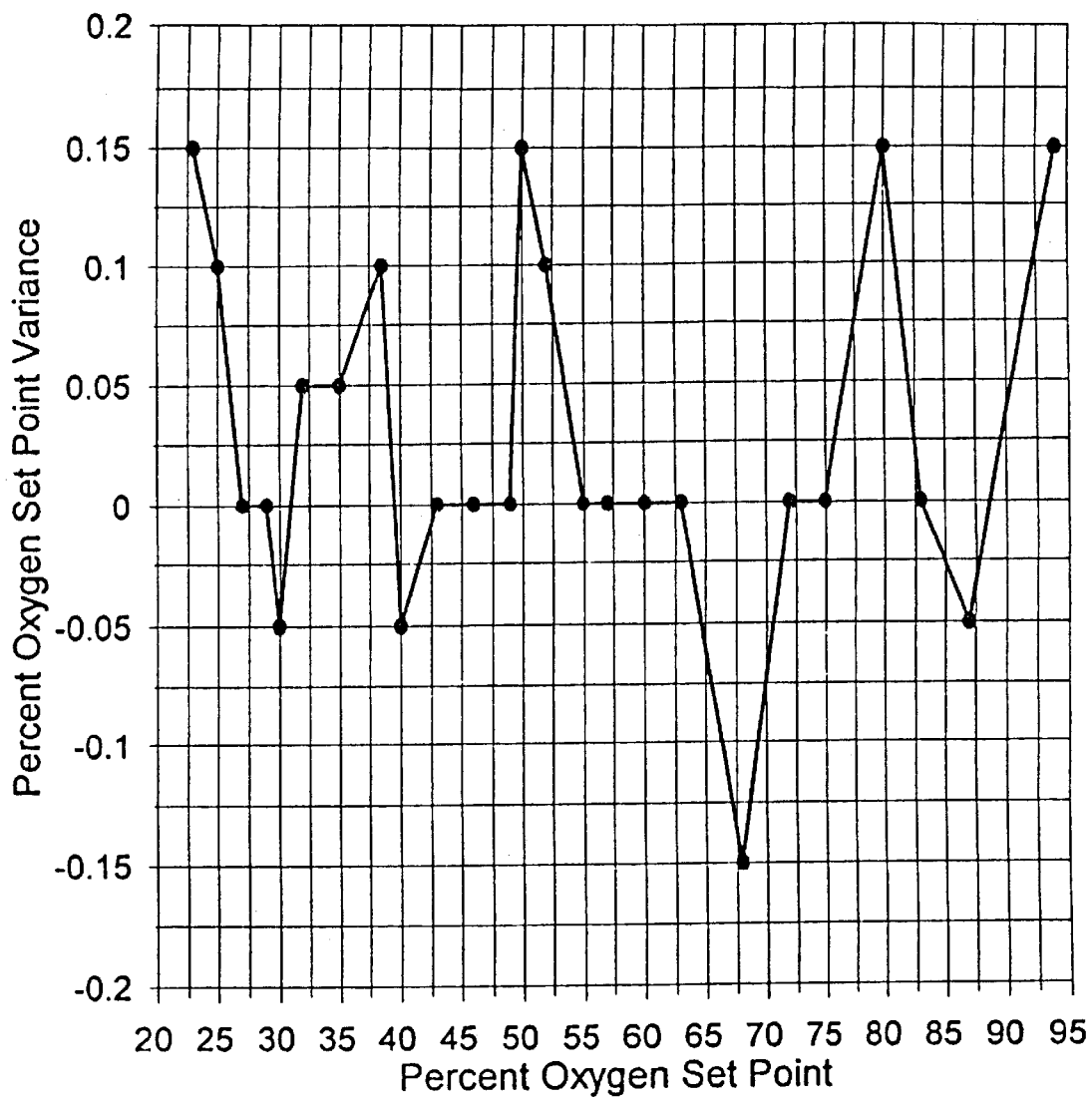
FIG. 4 is a graph showing percent variance in oxygen set point over a range of oxygen set points according to an actual prototype of the invention.

Actual test results from the prototype of the invention are set forth in Table 1, and plotted in FIG. 4.

TABLE 1

VARIABLE SET POINT OXYGEN CONCENTRATION MIXER DATA
Setup using 95% O2 and Air as the gas source

| Oxygen Set Point | Variance | Oxygen Reading |
|---|---|---|
| 23 | 0.15 | 23.15 |
| 25 | 0.10 | 25.1 |
| 27 | 0.00 | 27 |
| 29 | 0.00 | 29 |
| 30 | −0.05 | 29.95 |
| 32 | 0.05 | 32.05 |
| 35 | 0.05 | 35.05 |
| 39 | 0.10 | 38.06 |
| 40 | −0.05 | 39.95 |
| 43 | 0.00 | 43 |
| 46 | 0.00 | 46 |
| 49 | 0.00 | 49 |
| 50 | 0.15 | 50.15 |
| 52 | 0.10 | 52.1 |
| 55 | 0.00 | 55 |
| 57 | 0.00 | 57 |
| 60 | 0.00 | 60 |
| 63 | 0.00 | 63 |
| 68 | −0.15 | 67.85 |
| 72 | 0.00 | 72 |
| 75 | 0.00 | 75 |
| 80 | 0.15 | 80.15 |
| 83 | 0.00 | 83 |
| 87 | −0.05 | 86.95 |
| 94 | 0.15 | 94.15 |

The software (FIG. 3) in the mixer control board (11) adjusts the mixing valve switching times as follows: A predetermined total cycle time is set into the software, this total cycle time is then divided into smaller bits of time wherein these bits are chosen to be as small as the response time of mixing valve (5). This allows almost infinite adjustment of the mixing valve to control the gas concentration. Also, this increases the accuracy of the mixed gas.

More particularly, micro-controller 26 retains a count register in memory which contains a running value, designated herein as COUNTER. The value of COUNTER is updated (step 65 in FIG. 3) by either by incrementing the COUNTER value, or in the event the register contents has reached its final value (e.g. COUNTER=MAX) then resetting the COUNTER value to an initial value (e.g. zero). The oxygen purity set point is stored in micro-controller 26 and a variable value PWMVAL is calculated based on the desired set point to control switching of the valve (5) to obtain the desired oxygen concentration. Specifically, when COUNTER>PWMVAL the valve (5) allows air to flow into the mixing plenum (6) and when COUNTER<PWMVAL the valve (5) causes oxygen to flow. Therefore, if the oxygen concentration is less than the desired value PWMVAL is increased whereas if the oxygen concentration exceeds the desired value PWMVAL is decreased, thereby controlling the duty cycle of switching the valve (5) between air and oxygen, as discussed in greater detail below with reference to step 75. The COUNTER referred to in step 65 is a counter that keeps track of the pulse width value, so that an increase in COUNTER results in more time spent on the air side of the value.

At step 67, the keypad inputs 16A are scanned. If a key input is detected then the operator is led through a series of menus that allow for changing the set point, (e.g. oxygen set point, step 60). At an interval of 500 ms (step 69), the oxygen concentration is measured (step 71). Once every 1000 ms (step 72), the micro-controller 26 either increases the value of COUNT if the product gas is within the required tolerance of 0.25% (step 73) or decreases COUNT if the product gas is outside of the required tolerance. COUNT referred to in step 73 is a simple time delay count. When the gas is determined to be at purity, COUNT starts incrementing. This incrementing of COUNT (approximately 1 minute) allows time for the rest of the system to purge before delivering the gas. The product gas is output (in the case of the successful prototype, to a boost pump) when COUNT= MAX. If the oxygen concentration is out of range (i.e. COUNT=MIN), the product gas is purged via the exhaust port of product dump valve (15).

Next, a correction magnitude is computed using PID (Proportional Integral Derivative control) (step 75). The set point value (PWMVAL) is updated when necessary. The proportional integral derivative control algorithm calculates the magnitude of the error between the measured oxygen and the desired set point. The error is then subtracted from the current PWM setting to establish a new PWM setting.

Finally, an analog output and oxygen sensor bias voltage are updated via control 28, flags are set to update the display and new data is provided to the serial port 36 (step 77). The analog output is provided via a semiconductor chip on the circuit board that outputs a voltage from 0–1 volts DC corresponding to the oxygen concentration (e.g. 0.4 V=40% oxygen, 1 V=100% oxygen etc.) Alternatively, a voltmeter can be connected to monitor the concentration in the absence of an LCD. The board has several LED's that provide a quick visual indication that the board is operating; (e.g. LED's flash when the mixing valve is cycling or when the dump valve is energized). Also, there is a provision to run these LED signals to off-board LED's via a connector (not shown). Control then returns to step 63.

EPROM program memory 38, EEPROM programmable memory 40 and LED display drivers 42 are connected to micro-controller 26 in a well known manner.

While the oxygen sensor (10) and mixer control board (11) continue to compare detected purity concentrations and adjust the mixer valve (5) the mixed gas flows through the back pressure regulator (12) and into the product plenum (13). The mixed gas then flows through the orifice (14) and into the product dump valve (15). The product dump valve (15) is controlled by the mixer control board (11). The mixed gas through the product dump valve (15) is exhausted to atmosphere until the oxygen concentration is within the predetermined acceptable gas accuracy limit, as discussed above with reference to step 73. When the mixed gas is within the acceptable limit, the mixer control board (11) switches the product dump valve (15) and allows the gas to flow to the product out port of the product dump valve (15). If at anytime the oxygen sensor (1) senses that the mixed gas is not within the predetermined accuracy limit, the mixer control board (11) switches the product dump valve (15) back to the exhaust position thereby preventing unacceptable mixed product gas from being delivered by the device.

There are several significant design features of this device over previous gas mixer/blenders. The present invention allows the operator to simply set the desired oxygen concentration by means of a keypad and to quickly dial in gas concentrations ranging from 0% to 100% oxygen. The device automatically monitors and adjusts the oxygen concentration until the desired set point is achieved with no manual manipulation of the device, thereby increasing accuracy and eliminating operator error or errors due to sensitive, unstable mass flow controllers, mass weighing systems, partial pressure devices or manual flow controls. The device of the present invention automatically exhausts any gas that is not within the set point accuracy limits thereby ensuring that unacceptable product gas is not delivered. It accomplishes all of the foregoing with simple valves and oxygen monitors combined with a mixer control board.

Although the invention has been described in terms of the preferred embodiment described herein, those skilled in the art will appreciate other embodiments and modifications which can be made without departing from the sphere and scope of the invention. All such modifications are intended to be included with the scope of the claims appended hereto.

I claim:

1. Apparatus for mixing two gasses, at least one of which contains oxygen, to a desired concentration of oxygen, comprising:
   a) a mixing plenum;
   b) an inlet valve for admitting said two gasses into said mixing plenum;
   c) an oxygen sensor for detecting oxygen concentration of mixed gasses in said mixing plenum and in response generating an output signal representative thereof; and
   d) a controller for receiving said output signal and a user input representing said desired concentration of oxygen, comparing said oxygen concentration of said mixed gasses represented by said output signal to said desired concentration of oxygen represented by said user input, and in response controlling said inlet valve to regulate flow of respective ones of said two gasses into said mixing plenum and thereby maintain said desired concentration of oxygen.

2. The apparatus of claim 1, further comprising an outlet valve connected to said controller for receiving said mixed gasses from said mixing plenum and, under control of said controller, venting said mixed gasses in the event said oxygen concentration of said mixed gasses is outside of a predetermined range of tolerance from said desired oxygen concentration and outputting said mixed gasses in the event said oxygen concentration of said mixed gasses is within said predetermined range of tolerance from said desired oxygen concentration.

3. The apparatus of claim 2, wherein said controller maintains a counter register for cyclically counting from an initial value to a final value and calculates a further value based on a difference between said oxygen concentration of said mixed gases detected by said sensor and said desired concentration of oxygen, said further value being intermediate said initial value and said maximum value such that said controller causes said inlet valve to pass a first one of said gases containing oxygen when the value of said counter register is less than said further value and to pass a second one of said gases when the value of said counter register is greater than said further value, so as to minimize said difference over successive counting cycles of said counter register.

4. The apparatus of claim 3, wherein said controller maintains a further counter register for counting upwardly and downwardly between a maximum value and a minimum value based on a predetermined tolerance range of said concentration of said mixed gases detected by said sensor to said desired concentration of oxygen and increments said further counter register in the event said concentration of said mixed gases detected by said sensor is within said tolerance range and decrements said further counter register in the event said concentration of said mixed gases detected by said sensor is outside of said tolerance range and vents through said outlet valve said mixed gases in the event the value of said further counter register equals said minimum value and outputs said mixed gases in the event the value of said further counter register equals said maximum value.

5. The apparatus of claim 4, wherein said desired oxygen concentration is maintained within a tolerance range of 0.25%.

6. The apparatus of claims 2, 3, 4 or 5, wherein said mixing plenum further comprises a primary mixing plenum having an inlet connected to said inlet valve, a secondary mixing plenum having an inlet and an outlet, and an orifice intermediate an outlet of said first mixing plenum and the inlet of said second mixing plenum.

7. The apparatus of claim 6, including a further orifice connected between the outlet of said second mixing plenum and said oxygen sensor.

8. The apparatus of claim 6, further comprising a back pressure regulator a product plenum and an additional orifice connected in series intermediate said secondary mixing plenum and said outlet valve.

9. The apparatus of claim 1, wherein said controller maintains a counter register for cyclically counting from an initial value to a final value and calculates a further value based on a difference between said oxygen concentration of said mixed gases detected by said sensor and said desired concentration of oxygen, said further value being intermediate said initial value and said maximum value such that said controller causes said inlet value to pass a first one of said gasses containing oxygen when the value of said counter register is less than said further value and to pass a second one of said gases when the value of said counter register is greater than said further value, so as to minimize said difference over successive counting cycles of said counter register.

10. The apparatus of claim 1, further including a display for communicating said desired oxygen concentration and said oxygen concentration of said mixed gasses detected by said sensor.

11. Apparatus for mixing two gases, at least one of which contains oxygen, to a desired concentration of oxygen, comprising:
   a mixing plenum including a primary mixing plenum having an inlet connected to said inlet valve, a secondary mixing plenum having an inlet and an outlet, and an orifice intermediate an outlet of said first mixing plenum and the inlet of said second mixing plenum;
   an inlet valve for admitting said two gases into said mixing plenum;
   an oxygen sensor for detecting oxygen concentration of mixed gases in said mixing plenum and in response generating an output signal representative thereof;
   a controller for receiving said output signal and a user input representing said desired concentration of oxygen, comparing said oxygen concentration of said mixed gases represented by said output signal to said desired concentration of oxygen represented by said user input, and in response to controlling said inlet valve to regulate flow of respective ones of said two gases into said mixing plenum and thereby maintain said desired concentration of oxygen;
   an outlet valve connected to said controller for receiving said mixed gases from said mixing plenum and, under control of said controller, venting said mixed gases in the event said oxygen concentration of said mixed gases is outside of a predetermined range of tolerance from said desired oxygen concentration and outputting said mixed gases in the event said oxygen concentration of said mixed gases is within said predetermined range of tolerance from said desired oxygen concentration; and a back pressure regulator, a product plenum and an additional orifice are connected in series intermediate said secondary mixing plenum and said outlet valve.

12. The apparatus of claim 11 wherein said controller maintains a counter register for cyclically counting from an initial value to a final value and calculates a further value based on a difference between said oxygen concentration of said mixed gases detected by said sensor and said desired concentration of oxygen, said further value being intermediate said initial value and said maximum value such that said controller causes said inlet valve to pass a first one of said gases containing oxygen when the value of said counter register is less than said further value and to pass a second one of said gases when the value of said counter register is greater than said further value, so as to minimize said difference over successive counting cycles of said counter register.

13. The apparatus of claim 12, wherein said controller maintains a further counter register for counting upwardly and downwardly between a maximum value and a minimum value based on a predetermined tolerance range of said concentration of said mixed gases detected by said sensor to said desired concentration of oxygen and increments said further counter register in the event said concentration of said mixed gases detected by said sensor is within said tolerance range and decrements said further counter register in the event said concentration of said mixed gases detected by said sensor is outside of said tolerance range and vents through said outlet valve said mixed gases in the event the value of said further counter register equals said minimum value and outputs said mixed gases in the event the value of said further counter register equals said maximum value.

14. The apparatus of claim 13, wherein said desired oxygen concentration is maintained within a tolerance range of 0.25%.

15. The apparatus of claim 13, wherein said mixing plenum further comprises a primary mixing plenum having an inlet connected to said inlet valve, a secondary mixing plenum having an inlet and an outlet, and an orifice intermediate an outlet of said first mixing plenum and the inlet of said second mixing plenum.

16. A gas mixer for mixing two gases to a desired oxygen concentration level, at least one of the two gases including oxygen, comprising:

a first gas supply;

a second gas supply;

a mixing valve connected to said first gas supply and said second gas supply;

a mixing plenum connected to said mixing valve;

an oxygen sensor for detecting an oxygen concentration of the two gases mixed in said mixing plenum and in response generating an output signal representative thereof; and a controller for receiving said output signal and a user input representing said desired concentration of oxygen, comparing said oxygen concentration of said mixed gases represented by said output signal to said desired concentration of oxygen represented by said user input, and in response to controlling said mixing valve to regulate flow of respective ones of said two gases into said mixing plenum and thereby maintain said desired concentration of oxygen.

17. The gas mixer of claim 16, further comprising an outlet valve connected to said controller for receiving said mixed gases from said mixing plenum and, under control of said controller, venting said mixed gases in the event said oxygen concentration of said mixed gases is outside of a predetermined range of tolerance from said desired oxygen concentration and outputting said mixed gases in the event said oxygen concentration of said mixed gases is within said predetermined range of tolerance from said desired oxygen concentration.

18. The gas mixer of claim 17, wherein said controller maintains a counter register for cyclically counting from an initial value to a final value and calculates a further value based on a difference between said oxygen concentration of said mixed gases detected by said sensor and said desired concentration of oxygen, said further value being intermediate said initial value and said maximum value such that said controller causes said inlet valve to pass a first one of said gases containing oxygen when the value of said counter register is less than said further value and to pass a second one of said gases when the value of said counter register is greater than said further value, so as to minimize said difference over successive counting cycles of said counter register.

19. The gas mixer of claim 18, wherein said controller maintains a further counter register for counting upwardly and downwardly between a maximum value and a minimum value based on a predetermined tolerance range of said concentration of said mixed gases detected by said sensor to said desired concentration of oxygen and increments said further counter register in the event said concentration of said mixed gasses gases detected by said sensor is within said tolerance range and decrements said further counter register in the event said concentration of said mixed gases detected by said sensor is outside of said tolerance range and vents through said outlet valve said mixed gases in the event the value of said further counter register equals said minimum value and outputs said mixed gases in the event the value of said further counter register equals said maximum value.

20. The gas mixer of claim 16, wherein said controller maintains a counter register for cyclically counting from an initial value to a final value and calculates a further value based on a difference between said oxygen concentration of said mixed gases detected by said sensor and said desired concentration of oxygen, said further value being intermediate said initial value and said maximum value such that said controller causes said inlet value to pass a first one of said gasses containing oxygen when the value of said counter register is less than said further value and to pass a second one of said gases when the value of said counter register is greater than said further value, so as to minimize said difference over successive counting cycles of said counter register.

21. The gas mixer of claim 16, further comprising a second mixing plenum and an orifice connected to an outlet of said mixing plenum and an inlet of said second mixing plenum.

22. The gas mixer of claim 21, further comprising another orifice connected between an outlet of said second mixing plenum and said oxygen sensor.

23. The gas mixer of claim 21, further comprising a back pressure regulator, a product plenum and an additional orifice connected in series intermediate said second mixing plenum and said outlet value.

24. A method of mixing two gases to a desired oxygen concentration level, comprising:

supplying a first gas to a mixing valve;

supplying a second gas to the mixing valve;

flowing the first gas and the second gas through the mixing valve and mixing the first and second gases in a mixing plenum;

detecting an oxygen concentration level of the two gases mixed in the mixing plenum and in response generating an output signal representative thereof;

controlling the flow of the first gas and the second gas into the mixing plenum based on the output signal and a user input representing a desired concentration of oxygen by comparing the output signal against the desired concentration to maintain the desired concentration of oxygen.

25. The method of claim 24, comprising venting said mixed gases in the event said oxygen concentration of said mixed gases is outside of a predetermined range of tolerance from said desired oxygen concentration and outputting said mixed gases in the event said oxygen concentration of said mixed gases is within said predetermined range of tolerance from said desired oxygen concentration.

26. The method of claim 25, wherein said controlling step includes maintaining a counter register for cyclically counting from an initial value to a final value, and calculating a further value based on a difference between said oxygen concentration of said mixed gases detected by said sensor and said desired concentration of oxygen, said further value being intermediate said initial value and said maximum value such that said controller causes said inlet valve to pass a first one of said gases containing oxygen when the value of said counter register is less than said further value and to pass a second one of said gases when the value of said counter register is greater than said further value, so as to minimize said difference over successive counting cycles of said counter register.

27. The method of claim 26, wherein said controlling step includes maintaining a further counter register for counting upwardly and downwardly between a maximum value and a minimum value based on a predetermined tolerance range of said concentration of said mixed gases detected by said sensor to said desired concentration of oxygen, incrementing said further counter register in the event said concentration of said mixed gases detected by said sensor is within said tolerance range, decrementing said further counter register in the event said concentration of said mixed gases detected by said sensor is outside of said tolerance range, venting said mixed gases in the event the value of said further counter register equals said minimum value, and outputting said mixed gases in the event the value of said further counter register equals said maximum value.

28. The method of claim 24, wherein said controlling step includes maintaining a counter register for cyclically counting from an initial value to a final value, and calculating a further value based on a difference between said oxygen concentration of said mixed gases detected by said sensor and said desired concentration of oxygen, said further value being intermediate said initial value and said maximum value such that said controller causes said inlet valve to pass a first one of said gases containing oxygen when the value of said counter register is less than said further value and to pass a second one of said gases when the value of said counter register is greater than said further value, so as to minimize said difference over successive counting cycles of said counter register.

29. The method of claim 24, wherein the first gas and the second gas are alternatively supplied to the mixing value.

\* \* \* \* \*